United States Patent [19]

Galin

[11] 4,443,441
[45] Apr. 17, 1984

[54] FIXATION OF INTRAOCULAR LENSES

[76] Inventor: Miles A. Galin, 113 E. 39th St., New York, N.Y. 10016

[21] Appl. No.: 290,854

[22] Filed: Aug. 7, 1981

[51] Int. Cl.$^3$ .................. A61K 31/33; A61K 31/415; A61K 31/22; A61K 31/135

[52] U.S. Cl. ................. 424/244; 424/273 R; 424/273 B; 424/311; 424/330

[58] Field of Search ............... 424/311, 273 R, 273 B, 424/244, 330

[56] References Cited

U.S. PATENT DOCUMENTS 3,658,963  4/1972  Turner et al. ...................... 424/311

OTHER PUBLICATIONS

Wand et al.-Survey of Ophth. 25(2): 75-84 (1980),
"Thymoxamine Hydrochloride: An Alpha-Adrenergic Blocker".
Chem. Abst. 77, 654f (1972)—Fawke.
Chem. Abst. 78, 24240(q), (1973)—Hugues et al.
Chem. Abst. 85, 56925(c), (1976)—Wand et al.
Chem. Abst. 87, 177909(a), (1977)—Mayer et al.

*Primary Examiner*—Douglas W. Robinson
*Attorney, Agent, or Firm*—Brumbaugh, Graves, Donohue & Raymond

[57] ABSTRACT

The fixation of an intraocular lens is aided by instilling into an eye having an intraocular lens about one drop of an ophthalmic solution containing an α-adrenergic blocking agent, such as thymoxamine, in a concentration of from about 0.1% to about 1% by weight, preferably about 0.5% by weight.

5 Claims, No Drawings

FIXATION OF INTRAOCULAR LENSES

The present invention relates to the fixation of intraocular lenses.

An intraocular lens, when surgically implanted, is designed to replace a previously or simultaneously removed cataractous lens. There are various types of intraocular lenses, such as iris-supported lenses, anterior chamber lenses and posterior chamber lenses. The optical portion of such lenses may be of chemically pure polymethylmethacrylate or glass or any combination thereof. In an iris-supported lens the optical portion may have supports of the same nature, or may be supported by loops made of nylon, polypropylene or metal. Intraocular lenses, depending on the type, may be held in place by engagement of the loops with the iris, by angle fixation, by fixation in the lens capsular bag or by adhesions.

However, a pharmacological need exists for aiding the fixation of intraocular lenses, i.e., the maintaining or stabilizing in the correct position of intraocular lenses, the repositioning of partially dislocated intraocular lenses, and the ability to rapidly alter pupillary diameter in this regard. When pilocarpine was used as a potential fixation aid, it was found that pilocarpine causes spasms of the ciliary body termed "cyclotonia", intense constriction of the pupil through cholinergic stimulation of the sphincter muslce area, and poor and delayed reversibility. This firm contraction—squeezing on an intraocular lens—induces notching of the iris and atrophy of the sphincter area with iris-supported lens. In addition, the tight drum-like contraction precludes good fluid flow from the posterior and anterior chambers leading to debris depositing on the intraocular lens, and the potential for pupillary block, particularly with extracapsular cataract extraction. Further, the smaller pupil reduces vision, particularly in dim light.

Accordingly, it is the object of the present invention to aid the fixation of all types of intraocular lenses by compatible means.

It was found that this objective could be achieved by instilling into an eye having an intraocular lens about one drop of an ophthalmic solution containing an α-adrenergic blocking agent in a concentration of from about 0.1% to about 1% by weight. It is preferred that the ophthalmic solution contain the α-adrenergic blocking agent in a concentration of about 0.5% by weight. The approximately one drop dose can be repeated several times per day or daily, as may be necessary. Such instillation is easily reversible, permits pupillary response to light and dark and maintains passive miosis.

Suitable α-adrenergic blocking agents include tymoxamine (thymoxamine hydrochloride), phentolamine (phentolamine hydrochloride), azapetine (azapetine phosphate), phenoxybenzamine (phenoxybenzamine hydrochloride), clonidine (clonidine hydrochloride) and tolazoline (tolazoline hydrochloride). The preferred topical α-adrenergic blocking agent is thymoxamine and the preferred solvent is water.

The α-adrenergic blocking agent, such as thymoxamine, used to aid in the fixation of intraocular lenses act as a miotic and causes miosis or contraction of the pupil induced by paralysis or relaxation of the dilator muscle of the iris without contraction of the sphincter muscle of the iris. This unique pupillary activity reduces eccentric synechia formation and lens dislocation. It was further found that the α-adrenergic blocking agents are compatible with the materials from which the various types of intraocular lenses are made.

An aqueous ophthalmic solution containing about 0.5% by weight thymoxamine (available from William R. Warner & Co., Ltd., or Warner-Lambert Company) can have the following composition:

Thymoxamine Hydrochloride: 500 mg.
Sodium Acetate NF: 90 mg.
Boric Acid NF: 1610 mg.
Phenylmercuric Nitrate NF: 2 mg.
Purified Water USP q.s. to: 100 ml.

This aqueous ophthalmic solution can be prepared by dissolving the sodium acetate, boric acid and phenylmercuric nitrate in most of the purified water. Dissolution can be promoted by heating the solution. Upon cooling the solution to room temperature, the thymoxamine hydrochloride may be added and can be dissolved without further heating. The remainder of the purified water may then be added to reach a final volume of 100 ml. Sterilization of the solution can be achieved by filtering it through a sterilizing filter. This exemplary aqueous opthalmic solution has a pH of about 5.6–6 and is clear and colorless.

The process of the present invention has been satisfactorily used for aiding the fixation of all types of intraocular lenses in animals and humans.

Several advantages of using thymoxamine (or other α-adrenergic blocking agents) in the process of the present invention are noted below.

At the time of insertion of an intraocular lens in the operating room, it is desirable to dilate the pupil for posterior chamber lenses and for iris fixation lenses. Dilatation can be achieved with sympathomimetic agents and cholinergic inhibitors. The usual use of sympathomimetic agents is contraindicated, because after the procedure is finished, the pupil may dilate widely and, as a consequence, the lens may dislocate. The use of thymoxamine in the operating room to reverse the dilating effects of sympathomimetic agents is advantageous. Further, the use of thymoxamine in the placement of anterior chamber lenses where the pupil needs to be small during the insertion of the lens and wide after the insertion of the lens is advantageous, because of the ease of reversibility of the agent.

As mentioned above, the use of thymoxamine is not limited to iris-supported lenses. Posterior chamber lenses, for example, often need the pupil to be small for several days while the lens fixates itself, and the pupil may be dilated. Iris-supported lenses are probably best fixated by passive miosis so tht the pupil will move and notching will not occur.

The present invention also has the unique potential of a recently developed iris-supported lens being put in the eye, maintained in position by passive pupillary miosis, and then dilating the pupil so that the iris will come in front of the lens due to the contour of this lens. The passivity of the miosis precluding synechias, therefore, permits ultimate dilation and positioning of the iris in front of the lens.

What is claimed is:

1. A process for aiding the stabilizing or repositioning of a surgically implanted intraocular lens in the correct position in an eye, characterized by instilling into the eye having the surgically implanted intraocular lens an approximately one drop dose of an ophthalmic solution containing an α-adrenergic blocking agent selected from the group consisting of thymoxamine, phentolamine, azepetine, phenoxybenzamine, clonidine and totazoline in a concentration of from about 0.1% to about 1% by weight.

2. The process defined by claim 1, characterized by the α-adrenergic blocking agent is thymoxamine.

3. The process defined by claim 1, characterized by the aqueous ophthalmic solution contains thymoxamine in a concentration of about 0.5% by weight.

4. The process defined by claim 1, characterized by the approximately one drop dose is repeated several times per day.

5. The process defined by claim 1, characterized by the approximately one drop dose is instilled daily.

* * * * *